US011007244B2

(12) United States Patent
Bozinis et al.

(10) Patent No.: US 11,007,244 B2
(45) Date of Patent: May 18, 2021

(54) SOLUBLE, STABLE, ANTI-INFLAMMATORY, PROLIFERATIVE, PROTECTIVE AND MUCOADHESIVE PHARMACEUTICAL COMPOSITIONS; USE THEREOF FOR TREATING MUCOSITIS CONDITIONS AND METHOD FOR PRODUCING SAME; BASE PHARMACEUTICAL COMPOSITION FOR PREPARING THE PHARMACEUTICAL COMPOSITIONS AND METHOD FOR PRODUCING SAME

(71) Applicants: FBM INDÚSTRIA FARMACÊUTICA LTDA., Goiânia (BR); UNIVERSIDADE FEDERAL DE GOIAS, Goiânia (BR)

(72) Inventors: Marize Campos Valadares Bozinis, Goiania (BR); Eliana Martins Lima, Goiania (BR); Aline Carvalho Batista, Goiania (BR); Ricardo Neves Maretto, Goiania (BR); Elisamauro Francisco de Mendonça, Goiania (BR)

(73) Assignees: FBM INDUSTRIA FARMACÊUTICA LTDA., Goiânia (BR); UNIVERSIDADE FEDERAL DE GOIAS, Goiânia (BR)

(*) Notice: Subject to any disclaimer, the term of this patent is extended or adjusted under 35 U.S.C. 154(b) by 707 days.

(21) Appl. No.: 15/522,763

(22) PCT Filed: Oct. 27, 2014

(86) PCT No.: PCT/BR2014/050002
§ 371 (c)(1),
(2) Date: Apr. 27, 2017

(87) PCT Pub. No.: WO2016/065442
PCT Pub. Date: May 6, 2016

(65) Prior Publication Data
US 2017/0319642 A1    Nov. 9, 2017

(51) Int. Cl.
| | |
|---|---|
| *A61K 36/9066* | (2006.01) |
| *A61K 36/28* | (2006.01) |
| *A61K 9/00* | (2006.01) |
| *A61K 9/20* | (2006.01) |
| *A61K 31/045* | (2006.01) |

(52) U.S. Cl.
CPC .......... *A61K 36/9066* (2013.01); *A61K 9/006* (2013.01); *A61K 9/20* (2013.01); *A61K 9/2018* (2013.01); *A61K 9/2031* (2013.01); *A61K 9/2054* (2013.01); *A61K 31/045* (2013.01); *A61K 36/28* (2013.01)

(58) Field of Classification Search
None
See application file for complete search history.

(56) References Cited

U.S. PATENT DOCUMENTS

| | | | |
|---|---|---|---|
| 2011/0212142 A1* | 9/2011 | Chaniyilparampu | ........................ A61K 9/0048 424/400 |
| 2013/0052145 A1* | 2/2013 | Obwaller | ............. A61K 9/0031 424/49 |

OTHER PUBLICATIONS

Bastos, C., et al., Revista de Biotecnologia & Ciencia, vol. 1, No. 2. (Year: 2013).*
Dumortier, et al., Pharmaceutical Research, 23:2709. (Year: 2006).*
Avila, et al., 46° Brazilian Congress of Pharmacology and Experimental Therapeutics, "Mucoadhesive formulation containing *Bidens pilosa* L. (*Asteraceae*) reduces intestinal injury against 5-fluorouracil-induced mucositis in mice," 09.067. (Year: 2014).*
Bastos, CCC, "Effects of the mucoadhesive formulation of *Bidens pilosa* L. (*Asteraceae*) and *Curcuma longa* L. (*Zingiberaceae*) in the treatment of intestinal mucositis," 79f. Dissertation (Master in Pharmaceutical Sciences)—Federal University of Goiás, Goiânia. (Year: 2014).*
Ávila, PHM, "Action of the mucoadhesive formulation containing *Bidens pilosa* L (*Asteraceae*) on intestinal mucositis induced by 5-fluorouracil in mice," 69f. Dissertation (Master in Pharmaceutical Sciences)—Federal University of Goiás, Goiânia. (Year: 2013).*
Filho, EXDS, "Efeitos da fornnulagao mucoadesiva corn extrato de *Curcuma longa* L. em animais portadores de mucosite intestinal induzida por 5-fluorouracil," 90f. Dissertation (Master in Pharmaceutical Sciences)—Federal University of Goiás, Goiânia. (Year: 2014).*

* cited by examiner

*Primary Examiner* — Michael Barker
(74) *Attorney, Agent, or Firm* — Ditthavong, Steiner & Mlotkowski

(57) ABSTRACT

The present invention relates to pharmaceutical compositions with mucoadhesive and sustained release characteristics containing the association of the extract or fractions of *Curcuma longa* L. with curcuminoid content greater than 5% and *Bidens pilosa* (Bd) extract, which has an important proliferative and anti-inflammatory effect, for the treatment of inflammatory diseases of the oral cavity (stomatitis) and of the gastrointestinal tract, as, for example, mucositis induced by radiotherapy and/or chemotherapy and aphthous lesions. Additionally, inflammatory skin lesions and vaginal mucositis. These are compositions obtained from a liquid base formulation containing an aqueous-based solvent system. The subject of the present invention is, therefore, to obtain pharmaceutical preparations, to develop their obtainment processes and to establish their uses. These preparations contain an association between the *Bidens pilosa* (or its fractions) extract and the *Curcuma longa* (or its fractions) extract at 1:10 to 10:1 proportions, incorporated into semi-solid, liquid or solid pharmaceutical forms containing the synthetic or adhesive bio (mucus) component, diluents, carriers, binders, disintegrants, at the concentration ranges from 1 to 75% by weight, of the active agents of vegetable origin.

6 Claims, 3 Drawing Sheets

SOLUBLE, STABLE, ANTI-INFLAMMATORY, PROLIFERATIVE, PROTECTIVE AND MUCOADHESIVE PHARMACEUTICAL COMPOSITIONS; USE THEREOF FOR TREATING MUCOSITIS CONDITIONS AND METHOD FOR PRODUCING SAME; BASE PHARMACEUTICAL COMPOSITION FOR PREPARING THE PHARMACEUTICAL COMPOSITIONS AND METHOD FOR PRODUCING SAME

RELATED APPLICATIONS

This application is the national stage application of International Application PCT/BR2014/050002, filed on Oct. 27, 2014, the entire contents of which are hereby incorporated by reference.

FIELD OF THE INVENTION

The present invention relates to pharmaceutical compositions with mucoadhesive and sustained release characteristics containing the association of the extract or fractions of *Curcuma longa* L. with curcuminoid content greater than 5% and *Bidens pilosa* (Bd) extract for the treatment of inflammatory diseases of the oral cavity (stomatitis) and of the gastrointestinal tract, as, for example, mucositis induced by radiotherapy and/or chemotherapy and aphthous lesions. Additionally, inflammatory skin lesions and vaginal mucositis are the targets of therapy with the compositions in question.

BACKGROUND OF THE INVENTION

Mucositis induced by radiotherapy and/or chemotherapy is the most common complication in the treatment of malignant neoplasias, which affects 80 to 100% of patients. Mucositis is the most important acute side effect in the treatment of cancer. In patients undergoing radiation therapy with dose hyperfractionation the incidence is 100%, in conventional radiotherapy it reaches 97%, and when associated with chemotherapy it reaches 90%.

In cases of exclusive chemotherapy, the incidence reaches 22%. In bone marrow transplantation, the incidence of mucositis is 80 to 100%. The main clinical manifestations of mucositis include erythema, edema, bleeding, ulceration and pseudomembrane formation.

Ulcerations result in intense pain and almost always require nutritional support and analgesics through the parenteral route. Clinical evaluation and measurement of mucositis intensity are done using indexes proposed by WHO.

The difficulty of swallowing solid and liquid foods, limitation of speech and chewing, loss of weight and need for parenteral nutrition are complications resulting from mucositis. Another aggravating factor of mucositis is the susceptibility to infection by opportunistic microorganisms that invade damaged tissues predisposing them to severe infections and even sepsis, significantly increasing morbidity.

The painful component associated with the severity of mucositis may be sufficiently debilitating to cause a reduction of the proposed chemotherapy protocol and temporary or permanent interruption of radiotherapy.

Discontinuation of radiotherapy and changes in chemotherapy dose have been associated with increased tumor recurrence, with consequent decreased survival.

This complication results in hospitalization with increased cost of patient care. The treatments used for mucositis are palliative and diversified, involving prophylactic therapies and attempts to reduce pain.

Alternatives for the treatment of mucositis include the administration of antioxidants, such as amifostine, melatonin and allopurinol.

Mucosal protectors such as benzydamine sucralfate and anti-inflammatory drugs with anesthetic effect are also used.

However, a "gold standard" treatment for mucositis has not yet been established, and the development of new therapeutic resources that are effective and accessible to cancer patients and/or patients with an indication for bone marrow transplantation is extremely important.

Medications commonly used in cancer treatment, including methotrexate, which inhibits DNA synthesis, tend to produce mucositis. Similar effects are seen with alkylating agents, such as 5-fluorouracil, often used in the treatment of malignant tumors of the gastrointestinal tract.

The gastrointestinal cell destruction observed in the mucositis by antineoplastic and/or radiotherapy results from cell hypoproliferation, with villous atrophy, deepening of the crypts, resulting from absorption dysfunction, alteration in the secretion of electrolytes, mainly $Na^+$ and $K^+$, thus causing diarrhea.

Currently, some authors describe gastrointestinal mucositis as food mucositis, where it is observed inflammation, erosion and ulcerative lesions in the alimentary tract, secondary to cancer chemotherapy/radiotherapy or to previous procedures to bone marrow transplantation. In this context, vaginal mucositis in women has also been reported.

The mechanisms of food mucositis development and/or mucosal inflammatory processes have been described in four phases: initial period, restitution, inflammation, recovery. The initial phase occurs by the action of agents that block the synthesis of DNA by inhibition of topoisomerase and synthesis of the thymidylate. Alterations in the ribonucleic acid (RNA) molecule and formation of free radicals may also occur. These alterations inhibit mitotic processes, affecting cell integrity and provoking the influx of inflammatory and immune cells.

During the second phase, cell division stops for a few hours and apoptosis occurs. There is, therefore, an induction of the progressive loss of cells in the crypts, which activates the restitution processes. At this stage, there is a collapse in the depth and number of crypts, shortening of villi and depletion of goblet cells. This phase is characterized by fluid losses and bacterial colonization.

Finally, in the recovery process there is a significant cellular proliferation, which leads to the functional restoration of crypts and/or tissues. Therefore, there is a recovery of the tissue structures, such as villi, and the recovery of the absorptive surface of the intestine.

Apoptosis, or programmed cell death, in intestinal mucositis, may be physiological or induced by chemotherapy or radiotherapy. The large number of apoptotic cells generated in the intestinal crypt was observed in mice receiving chemotherapy and in intestinal biopsy samples from tumor patients who received antineoplastic treatment.

Previous studies (Sonis et al., 2004, Carl, 1995, Pico et al., 1998, Köstler et al., 2001, Epstein and Schubert 2003, Sonis, et al., 2004; Armstrong and McCaffrey, 2006) have considered that the genesis of chemotherapy-induced intestinal mucositis was correlated with apoptotic effects of cytotoxic drugs on small intestinal cells.

As an example, one can highlight cytotoxic drugs causing apoptosis in stem cells in the crypt of the small intestine, which inhibited the regeneration of the same and, therefore, created a deficit in the number of stem cells. This deficit generated morphometric alterations such as villus atrophy and crypt hypoplasia in the intestine. Thus, apoptosis plays a critical role in chemotherapy-induced mucositis.

Therefore, one of the purposes of this invention is to provide a composition which exerts inhibitory and/or controlling action on chemotherapy-induced intestinal apoptosis.

The mechanism of induction of small cell intestinal apoptosis by chemotherapy is still uncertain but may be correlated with the release of pro-inflammatory factors such as IL-1β due to pathophysiological changes of the intestinal mucosa that received chemotherapy.

Studies have shown that IL-1β has its expression significantly increased in the intestinal mucosa tissue of rats receiving chemotherapy. High IL-1β expression was also observed in animal model peripheral blood serum receiving chemotherapy (Wu et al., 2011; Wu et al., 2010).

Although IL-1β is involved in the inflammatory reaction of the organism, other studies have found that this cytokine could induce the apoptosis phenomenon in several cell types. Induction of apoptosis in various cell types occurs because IL-1β is involved in the activation of several apoptosis-related factors, such as Bax and Bcl-2 (Meirovitz, et., 2010).

The process of intestinal apoptosis induced by chemotherapy was accompanied by increased regulation of pro-apoptotic factors (Bax, Caspase-3, Bak, and P53) and decreased regulation of anti-apoptotic factors (Bcl-2 and Bcl-XL) in Small intestinal crypt cells, which led to the genesis of intestinal mucositis in small cells. Therefore, IL-1β is possibly involved in apoptosis of small intestinal crypt cells after chemotherapy.

The interleukin-1 receptor antagonist (IL-1Ra) is a naturally occurring protein that has antagonistic biological effects of IL-1, which may antagonize the inhibitory role of IL-1 on endothelial cell proliferation and promote cell growth endothelial cells through receptor binding of interleukin-1 (IL-1R). Several studies also report the inhibitory role of IL-1Ra in cellular apoptosis in different experimental models (wu, et al., 2011; Yoshida, et al., 2006).

Studies suggest that the strong increase of IL-1β in the body after chemotherapy may be involved in the activation of the apoptosis process of small intestine cells (Vissink et al., 2003; Peterson, 1999; Fall-Dickson, et al., 2007; Logan, et al., 2007).

In this context, it is important to note that several studies (Vathsala, et al., 2012; Lüer, et al., 2011) have reported on the immunomodulatory action of curcumin. Among these, some authors reported their important anti-IL-1 action.

Stomatitis is defined as any inflammatory process affecting the oral cavity. Inflammatory lesions may have several etiologies: infectious, autoimmune, traumatic, neoplastic or drug reactions. They may be presented as isolated lesions, being a local manifestation of a systemic disorder or they can be originated from the local commitment, leading, eventually, to the general affection of the individual. Oral lesions are classified according to their macroscopic appearance as white lesions, vesico-bullous, aphthous and tongue lesions.

The macroscopic aspects of the lesions are related to their etiology, for example: white lesions are associated with candidiasis, leukoplakia, lichen planus, Fordyce granules, nicotinic stomatitis, hairy leukoplakia, secondary syphilis; vesico-bullous lesions are associated with herpes simplex, herpes zoster, pemphigus, pemphigoid, erythema multiforme, Stevens-Johnson syndrome; aphthous lesions are related to recurrent atopic stomatitis, Behget's disease, systemic lupus erythematosus, mucositis, chemical burns, orthodontic appliance trauma; tongue lesions are related to fissured tongue, benign migratory glossitis (geographic tongue), median rhomboid glossos, glossodinea.

Oral ulcers, also called aphthous ulcers, atopic stomatitis or simply canker sores, are very common lesions of the oral mucosa with an inflammatory background, affecting about 20% of the population. Canker sores are usually benign lesions that do not usually cause more problems than discomfort, however, some more serious diseases of the oral cavity may manifest with very similar ulcerated lesions. An example is cancer of the oral cavity, which in the early stages may look like a cold sore. Canker sores that take more time to heal are those that appear in places where there is constant contact with teeth or with food, suffering repeated trauma throughout the day. Some people have large canker sores, called major canker sores, larger than 1 cm and deep. These take up to six weeks to disappear and can leave a scar. There is also the herpetiform canker sore, formed by multiple small ulcers that come together and become a larger lesion. These canker sores may be accompanied by lymph nodes in the neck (tongues) and sometimes of low fever and malaise.

The aphthous lesions appear to be caused by an imbalance of the immune system. Some of the known triggers are: local trauma, such as accidental bites; psychological stress; few hours of sleep; *Helicobacter pylori*, the same bacteria that causes gastric ulcer; some toothpaste containing sodium lauryl sulfate; gastroesophageal reflux; foods like chocolate, coffee, soft drinks, tomatoes and pineapples; cigarette; hormonal changes during the menstrual cycle; deficiency of some vitamins and minerals such as vitamin B12, vitamin C, zinc, iron or folic acid; drugs such as anti-inflammatories, rapamycin, methotrexate, aspirin and atenolol. Usually, oral ulcers caused by systemic diseases are multiple and recurrent. They usually have some different characteristics of common canker sores and are accompanied by other symptoms. In cases of lupus, canker sores are often painless and accompanied by skin lesions and joint pain, as well as systemic symptoms such as low fever and tiredness. In Behcet's disease, also an autoimmune disease, aphthae are multiple, recurrent and accompanied by ulcers also in the genitals. Eye injuries are also common. In celiac disease and Crohn's disease, canker sores come in conjunction with intestinal symptoms such as diarrhea and blood in the stool. Neutropenia, which is the fall in the number of neutrophils in the blood, is also a cause of oral ulcers. It is usually seen in patients undergoing chemotherapy but may occur in any disease or drug that causes neutropenia.

Various infections can cause mouth ulcers like canker sores:

The HIV virus can cause oral ulcers in advanced stages (when there are already criteria for AIDS) and in the acute phase of virus infection. Infection with Coxsackie virus (herpangina), very common in children, can result in sore throat, fever, small oral ulcers and lesions on the palms and soles of the feet. Syphilis, both the primary and secondary phases, can result in oral ulcers. These ulcers are usually multiple and in the secondary phase they take a long time to heal. Herpes labialis presents as vesicles that can become small ulcers after they rupture. The appearance is not much like sore throat, but can be confused by lay people. Some cancers of the oral cavity may present as ulcerations, being initially confused with common canker sores.

In addition to lesions of the oral cavity associated with inflammatory processes, cutaneous lesions caused by several etiologies, such as diabetic foot, are common and treated with substances with anti-inflammatory/proliferative potential to promote tissue repair. Among the manifestations of practically all skin diseases, the occurrence of several types of lesions that alter the appearance of the skin stands out. The cutaneous lesions are very distinct, for example, maculas, papules, loss of tissue, vesicles, blisters, pustules, crusts, among others.

Curcumin and related substances (curcuminoids) are phenolic compounds of low molecular weight characterized by yellowish coloration and which originate from the rhizome of the *Curcuma longa* L. plant. In Asian medicine the curcuminoids of *Curcuma longa* L have been used for generations for the treatment of many diseases including inflammation, skin sores, liver and biliary disorders, cough as well as tumors. *Curcuma longa* is reported in the literature as safe for human use (Dadhaniya, et al., 2011).

In the present invention, the term "curcumin" is understood as the substance of molecular formula $C_{21}H_{20}O_6$ of high purity or in admixture with other curcuminoids present in the roots of *Curcuma longa* L. in different proportions, as well as in other plant species.

Likewise, in the present invention, the term "*Bidens pilosa*" extracts is understood to mean all preparations derived from the different parts or whole, whether or not pre-processed, of the species *Bidens pilosa*. These extracts can be obtained from conventional extraction processes, such as maceration, percolation and others, as well as from non-conventional extraction processes, such as extraction by ultrasound, microwave, supercritical fluid, among others. The use of atomized dried extracts, lyophilized or concentrated extracts or fractions purified by various methods is also considered.

It is therefore another subject of this invention, the utilization of *Curcuma longa* in compositions, acting as an immunomodulatory agent in view of its anti-IL-1 action.

*Bidens pilosa* (Bd) is a Brazilian plant popularly used in the form of teas for the treatment of liver diseases. It has proven anti-inflammatory, antioxidant, antiallergic, antimicrobial, healing and fibroblast inducing action.

The state of the art demonstrates that clinical studies have proven that Bd can promote the recovery of mucosal lesions. In parallel, randomized controlled double-blind clinical studies of the preparation containing Bd demonstrated an antiallergic effect of the same without clinical toxic effects (Corren et al., 2008). Preclinical toxicological studies have demonstrated that Bd does not present genotoxicity (Costa et al., 2007).

It is therefore a further subject of the present invention to provide a composition made from preparations containing *Bidens pilosa* (Bd), free of toxic effects and promoting various actions, in preparations employed to promote the recovery of cutaneous and mucous membranes lesions.

The use of plant resources is a strategy of great relevance for the development of new drugs, since these materials may present unique biological activities due to the associated action of different substances, which sometimes act through different and complementary mechanisms of action. The use of these materials may, in certain cases, be considered safer in relation to drug therapy with synthetic drugs.

However, there are numerous technological challenges related to the development of pharmaceutical products that contain complex mixtures of natural substances.

In fact, standardization, ensuring the stability and effectiveness of these preparations is a complex task that requires innovative development.

Previous attempts were made using associations of natural substances, among which we can highlight curcumin, a phenolic antioxidant extracted from the rhizome of the *Curcuma longa* plant. Such prior efforts may be represented by document WO200388986, published on Oct. 10, 2003, which relates to a combination of curcumin with an antioxidant and at least one edible oil used for the prevention and treatment of tissue damage of patients undergoing radiation therapy. Basically, priority refers to the prevention and treatment of damage to the tissues of a patient undergoing radiotherapy in laryngeal, esophagus, oral cavity, nasopharyngeal cancer treatment, resulting in radiation-induced mucositis.

The reference proposes the use of curcumin oil, associated with an antioxidant, and an edible oil, preferably a vegetable oil, such as sunflower oil, and preferably, being chosen as the antioxidant vitamin "E" or α-tocopherol.

Thus, it can be observed that the priority does not anticipate or suggest the use of a preparation based on the association of *Curcuma longa*, in the form of extract or fraction or isolated substance, with extracts of *Bidens pilosa*.

Unexpectedly, it has been observed that the associated action of *Bidens pilosa* (Bd) and *Curcuma Longa* could be advantageously employed to produce a preparation used in the production of a safe, nontoxic drug with useful pharmacological properties, capable of promoting the recovery of Lesions of the mucosa and tissues with inflammatory processes.

In the present invention, a preparation in which *Bidens pilosa* (picão preto) was used as a glycerol extract, which was formulated together with the extract or fraction of *Curcuma longa* extract having curcuminoids content greater than 5%.

Curcumin, the main representative of curcuminoids, is a phytopharmaceutical extracted from the roots of *Curcuma longa* L., which presents numerous therapeutic activities, among them, the activities chemoprotective, antioxidant, antimicrobial and anti-inflammatory.

Curcumin is the most abundant curcuminoid in the roots of *Curcuma longa*. Phenyl, hydroxylic and methyl groups are related to the biological actions of this substance.

Some aspects of great relevance should be considered to ensure proper use of this compound. A relevant problem which lacked adequate solution in the state of the art in order to obtain a composition promoting the association of the planting agents of the present invention lies in the fact that curcumin has reduced aqueous solubility in pH-media Acid and degrades rapidly in media with alkaline pH.

Its solubility/stability behavior hampers the effective administration of this substance, particularly because of its low aqueous solubility, greatly hindering the development of a medicament to be administered orally, with easy absorption and assured stability.

Therefore, it is very important, and it is a major object of the present invention to provide a composition for the prevention and treatment of inflammatory diseases, for example mucositis, capable of employing curcumin in aqueous base preparations having therapeutically suitable concentrations and Considerable stability.

Similarly, it is important to ensure proper dissolution of such substance from solid dosage forms such that the bioavailability of the drug preparation in solid form is adequate.

The extractive preparations obtained from *Bidens pilosa* represent other material of natural origin of great importance and that has attracted attention of the scientific community.

There are many traditional uses of these extracts, including the fight against malaria, hepatitis, laryngitis, headaches and gastric problems.

The extracts obtained from *Bidens pilosa* (Bd) have proven antibacterial, antioxidant and immunomodulatory action. Some of these activities are probably related to the presence of flavonoids in *Bidens pilosa* extracts.

Other classes of secondary metabolites are also present in the extracts, for example alkaloids, saponins, triterpenes and polyacetylenes. The biological activities of *Bidens pilosa* (Bd) are very promising and numerous patents have been deposited protecting its use as herbicide, anti-inflammatory, cosmetic and in the treatment of metabolic syndrome.

Because of the complex composition of plant extracts and the special solubility and stability characteristics of curcumin, the combination of such agents in stable and effective formulations requires innovative technological development which is one of the main aspects of the present invention.

In addition, the formulations used in the treatment of mucositis should have characteristics that aid in therapeutic success, such as high retention, penetration and stability in the environment, for example the oral, cutaneous or gastrointestinal environment.

The present invention has demonstrated the scope of a composition with novel features containing the association of *Curcuma longa* (its extracts or fractions) associated with the glycerinated extract of Bd which has an important proliferative and antiinflammatory effect, and correlated formulation with results superior to the effects of these substances when Evaluated separately in animals exposed to 5-fluoracil.

Mucositis is an inflammatory condition of the mucosa, which is atrophic, swollen, erythematous and sometimes ulcerated. This condition is almost, but not exclusively, invariably observed in cancer patients undergoing radiotherapy and chemotherapy.

Inflammatory lesions on the mucosa lead to a drastic reduction in patients' quality of life and may prevent the continuation of radiotherapy or chemotherapy. In addition, the colonization of inflammatory lesions ulcerated by opportunistic pathogens, particularly the oral cavity, can lead to sepsis and death.

Due to the recognition of its importance, academic and clinical efforts have been made to improve prevention and treatment of mucositis. Despite this, prophylactic and therapeutic strategies are still very limited.

Treatments based on reliable clinical evidence can still be considered as scarce. Some prior art procedures and related medicaments with adequate clinical evidence may be used as adjuvants in the mucositis tables caused by cytotoxic chemotherapy, such as, for example, in bone marrow pre-transplantation conditioning.

The use of palifermin (fibroblast growth factor KGFF1) has recently been approved for this. The clinical benefit of cryotherapy has also been demonstrated in these cases.

On the other hand, despite the aforementioned drugs that help reduce the suffering of patients with mucositis, on the other hand, specific drugs are still not available for the treatment and/or prevention of radiotherapy-related mucositis, with curative results Of this condition.

The preparations used in the clinic are currently not registered for this purpose and/or have no use based on reliable clinical evidence.

More particularly, reliable pharmaceutical preparations consisting of the combination of glycerinated extract of *Bidens pilosa* and *Curcuma Longa*, extracts thereof or fractions thereof, with adequate aqueous solubility and stability have not been developed and therefore do not appear in the state of the art. Present effectiveness in the treatment of mucositis in patients with cancer diagnosis, under radiotherapeutic and chemotherapeutic treatment.

Within this context, it is evident the need to develop new drugs that specifically act in the prevention and/or treatment of the various mucositis.

It is therefore an object of the present invention to provide pharmaceutical compositions containing the combination of *Bidens pilosa* extract and *Curcuma longa* extract (or fractions thereof) in proportions of 1:10 to 10:1, incorporated in semisolid pharmaceutical forms, Liquids or solids containing natural or synthetic bioadhesive components, diluents, carriers, binders, disintegrants, in the concentration ranges from 1 to 75% by weight, of the active agents of vegetable origin.

It is an object of the present invention to provide bioadhesive extended release systems which ensure the solubility and stability of the various incorporated active principles.

It is yet a further object of the present invention to provide a method of producing such pharmaceutical forms/delivery systems.

It is an object of the present invention to provide methods for the prevention and treatment of inflammatory, infectious, irritative, ulcerated or non-ulcerous conditions affecting the mucosa of the digestive tract, especially the buccal mucosa, as well as other mucous membranes of the human organism or Other mammals, such as the rectal, vaginal and nasal mucosa.

DESCRIPTION OF THE INVENTION

Figure 1:
FIG. 1—Formulation PI01. Body of background consisting of curcuminoids.

The starting liquid formulations of the present invention constitute the base element for the preparation of different pharmaceutical or cosmetic forms, such as mouthwash, mouthwash, drops, syrups, elixirs, among others for internal or external use.

In a first embodiment of the present invention, a liquid base formulation was prepared, and in the pharmaceutical forms derived therefrom, a block copolymer selected from poly (oxyethylene), poly (oxypropylene), poloxamer 407, or poloxamer 188, which was used because of its mucoadhesive and solubilizing properties.

In another aspect, the present invention relates to the preparation of multiparticulate polymer systems containing curcumin at a concentration of 1 to 50% by weight. Such systems are comprised of at least one bioadhesive natural polymer. They are also composed of a polymeric or lipid component capable of releasing the active principle in a prolonged manner on the surface of the mucosa.

Solvents such as distilled water, propylene glycol and polyethylene glycol 400 were used as carriers and as solubilizers.

Antioxidants such as butylhydroxytoluene, sodium bisulfite and sodium metabisulfite were used to maximize the oxidative stability of the formulations in the usual amounts of 0.01 to 1% v/v of the formulations.

Development of Liquid Formulations

The following description relating to the preparation of the liquid base formulation of the present invention presents both the formulations which constitute the novel element of the present invention but also includes those steps which, by their unsatisfactory result, demonstrate the actual effectiveness of what has been successfully developed by the inventors of the present invention.

Initially, formulations containing distilled water or a mixture of water and propylene glycol (1:1, v/v) were prepared at room temperature with mechanical stirring (500 rpm).

The addition of the curcuminoids in these formulations was carried out under constant mechanical agitation and the solutions obtained in this way had a concentration of less than 2.5 mg/mL. The addition of poloxamer to this blend greatly increased the dissolution of the curcuminoids. Incorporation of 15% (w/v) of this polymer into a water:propylene glycol (1:1) mixture led to improved solubilization of the curcuminoids in the preparation.

On the other hand, it was verified that the solutions obtained after the incorporation of 15% (w/v) of poloxamer still had concentration of curcuminoids of less than 2.5 mg/mL, showing that the procedure was still unsatisfactory. By directly adding the poloxamer to propylene glycol, a coarse dispersion has occurred which can not be used for the medicinal purposes for which the preparation is intended.

It is therefore concluded that as a first step in the process of preparing the liquid base formulation for the preparation of different pharmaceutical or cosmetic forms, such as mouthwash, mouthwash, drops, syrups, elixirs among others, for internal or external use, the basis of curcuminoids, is constituted of:

$1^{st}$ stage—Preparation of formulations containing distilled water or a mixture of distilled water and propylene glycol at 1:1 v/v at room temperature under mechanical agitation (500 rpm);

$2^{nd}$ stage—The curcuminoids is added under constant mechanical agitation, obtaining a solution with curcuminoids concentration of less than 2.5 mg/mL;

$3^{rd}$ stage—Adding poloxamer to the water mixture with propylene glycol and curcuminoid;

The procedure of incorporating the poloxamer into the mixture included dividing its total mass into two equal parts, followed by adding them to water and with propylene glycol. After the dispersion of poloxamer, the fractions were mixed under mechanical agitation and the resulting formulation showed good physical appearance, but as discussed above, it was not able to dissolve entirely the curcuminoids (see formulation PI01, FIG. 1).

4th stage—Adding to the mixture of water with propylene glycol, curcuminoid and poloxamer, with a co-solvent;

Aiming to increase the amount of curcuminoids dissolved, another co-solvent (polyethylene glycol 400, PEG 400) was added to the formulation (formulation PI02).

In this new formulation, the PEG 400 concentration was 20% (v/v), and it was incorporated at the expense of reducing the amount of water in the formulation (from 50% to 30% of the total volume).

Figure 2:
FIG. 2—Formulation PI02. Effect of the addition of polyethylene glycol 400.

FIG. 2 shows the improvement from the addition of this constituent. Thus, the ternary water mixture:PEG 400:propylene glycol (30:20:50, v/v/v) containing poloxamer (15%) could solubilize most of the mass of curcuminoids added (2.5 mg/ML). However, visual inspection showed the presence of small amount of precipitated material (FIG. 2, formulation PI02).

—Correction of the Solvent System of the $4^{th}$ Stage—

To further increase the solubility of the curcuminoids in the formulation, another modification was made to the composition of the solvent system, which now contained a larger amount of PEG 400 (30%, v v). This increase occurred at the cost of a further reduction in the amount of water in the preparation to 20% (v/v) (formulation PI03). This new change allowed total solubilization of the mass of curcuminoids added and the resulting solution contained 2.5 mg/ml of curcuminoids. The preferred solvent system in this base formulation is expressed below:

(1) propylene glycol from 45%-55%, plus preferably, 50%;
(2) polyethylene glycol 400, 25%-35%, plus preferably, 30%;
(3) purified water, 15%-25%, plus preferably 20%.

The poloxamer polymeric surfactant was added at the concentration of 15% (w/v), according to the procedure described above.

The PI03 formulation represented the starting point for the development of solutions with a higher concentration of curcuminoids and for those containing curcuminoids and *Bidens pilosa* extract, as described below.

Thus, the preferred, preferred base formulation of the present invention is composed of:

Curcuminoids—2.5 mg/mL and solvent system, preferably consisting of:

| | |
|---|---|
| Solvent - propylene glycol | 50% v/v |
| Co-solvent - polyethylene glycol 400 | 30% v/v |
| Surfactant - poloxamer | 15% p/v |
| Carrier - purified water | 20% v/v |

Development of Formulations Containing Curcuminoids and *Bidens pilosa*

Initially, it was observed that for the preparation of liquid compositions prepared from a synergistic mixture containing the combination of the liquid base formulation with *Curcuma Longa* extract and *Bidens pilosa* extract, by adding higher concentrations of curcuminoids (7.5 mg/ML) to the PI03 formulation, a large amount of precipitate is formed. This caused the alteration of the preparation technique of the composition of the present invention, as punctuated below.

(1) A mixture of PEG 400 was prepared with propylene glycol and this mixture was heated with the aid of a hotplate maintained at 65° C.;
(2) The poloxamer mass of the formulation was divided in equal parts and one of the parts was dispersed in the propylene glycol and heated PEG-400 mixture—STAGE I;

(3) The curcuminoids were then added to the mixture under mechanical stirring (500 rpm) for 30 minutes, still under heating (65° C.);

(4) The other half of the poloxamer mass was added in the aqueous phase at room temperature—STAGE II.

(5) After complete dispersion, the solution of Phase II was poured into the mixture of STAGE I, containing propylene glycol and PEG 400. STAGE III (6) The final mixture was then kept under stirring until the temperature reached 25° C. (approximately 30 minutes).

By the application of this new procedure, it was possible to dissolve up to 25 mg/mL of curcuminoids in the preparation, which remained physically stable for prolonged time at room temperature and was denominated as formulation PI04.

The incorporation of the *Bidens pilosa* extract into the PI04 formulation was carried out by replacing the entire distilled water mass and 20% of the propylene glycol mass by the glycerinated vegetable extract.—STAGE IV.

Therefore, this formulation, referred to as CBd, contains:

(1) propylene glycol, 30% (v/v);
(2) polyethylene glycol 400, 30% (v/v);
(3) glycerinated extract of *Bidens pilosa*, 40% (v/v).

In addition to these liquid components, the formulation contains the polymeric mucoadhesive agent (poloxamer, 15%, w/v), as well as sodium bisulphite and butylhydroxytoluene in usual concentrations. The preparation method of the CBd formulation was the same as described above for the PI04 formulation.

The active principles of the present invention have been successfully associated with the CBd formulation. No precipitation, cloudiness, lump formation, gelling or any other sign of incompatibility between the active ingredients were observed. In addition, the bioadhesive component was successfully incorporated in the presence of *Bidens pilosa* extract constituents.

The stability of these formulations was evidenced using an accelerated stability protocol, showing that the decay in the concentration of curcuminoids and total polyphenols was within the legally established limit. The remaining percentage of curcuminoids after 180 days of testing was 92.25% and the percentage of total polyphenols was 96.20% in relation to the initial content.

Preparation of a Semi-Solid Formulation Containing Curcuminoids and *Bidens pilosa*

The development of the semi-solid formulation was carried out aiming the preparation of a cream gel-type base, containing in the oil phase, in amounts ranging from 10 to 14.75% w/w of the total formulation of the oily components, and containing the following components in the amounts Preferential:

(1) liquid vaseline (5%, p/p);
(2) stearic acid (3%, p/p);
(3) cetyl alcohol (0.4%, p/p);
(4) cetostearyl alcohol (0.35%, p/p);
(5) monoestearato de glicerila (3%, p/p);
(6) isopropyl myristate (1%, p/p).

Poloxamer (15%, w/w) and propylene glycol (6%, w/w) were added to this phase. As preservatives methylparaben (0.1%, w/w), propylparaben (0.05%, w/w) and butylhydroxytoluene (0.05%, w/w) were used. All components of the oil phase were added to a jacketed vessel, and the temperature of the mixture was raised to 75° C. After the mixture reached the required temperature for the complete melting of the solids, curcuminoids were added to a final concentration of 25 mg/mL. After this addition, a new period of mechanical agitation (500 rpm) was followed until the entire mass of curcuminoids was dissolved in the oily base.

In a second jacketed vessel, the *Bidens pilosa* glycolic extract (65%, w/w) was heated to a temperature of 75° C. The aqueous extract was then poured onto the oily phase under constant mechanical stirring (500 rpm). After the mixture was complete the heating was switched off and stirring was continued until the resulting product reached room temperature (about 25° C.).

Preparation of a Solid Formulation Containing Curcuminoids and *Bidens pilosa*

Solid formulations, which may be tablets, tablets or capsules, and more preferably in tablet form, have been developed using mannitol as diluent and poloxamer as a mucoadhesive agent. The granulation liquid used was the *Bidens pilosa* extract itself at the rate of 35 to 45% w/v. The mass of each component of the blend is expressed as follows: (1) Curcuminoids (25-200 mg per tablet); mannitol (250 to 350 mg per tablet); poloxamer (100 to 140 mg per tablet); Microcrystalline cellulose (200 to 400 mg); Sodium metabisulfite (5 to 15 mg) and citric acid (20 to 40 mg.

Nine hundred and thirty grams of the above-described blends were inserted into the processing chamber of a fluidized bed apparatus for performing mixing and granulation operations.

The mixing step of the powders was initiated by the injection of heated air (45-65° C.) at a flow rate of 15 to 25 $m^3$ per hour for a period of 10 to 15 minutes. After the mixing step, the granulation liquid was added thereto in three steps. Between each of the granulation steps a drying step was performed (maintenance of the fluidization conditions without addition of liquid). All powders were sieved in stainless steel screens (250 micrometer aperture mesh) prior to performing the blending operation.

The granules were compressed in a rotary compression machine equipped with a table containing 8 sets of punches (numbers 13 to 15, depending on the formulation). The hardness of the tablets was determined during the process.

In Vitro Evaluations of Mucoadhesive Formulations Containing Curcuminoids, Bd and Their Association.

Studies conducted by the inventors of the present invention have demonstrated that the association of the *Curcuma longs* fraction with curcuminoids content greater than 5% to the glycerinated extract of Bd showed an important hyperproliferative and anti-inflammatory effect superior to the effects of these substances when evaluated separately in animals exposed to 5-fluoracil. A protective effect against 5-fluoracil (5-FU)-induced mucositis was observed to be superior to the protective effect of curcuminoids or Bd evaluated separately, both prophylactically and therapeutically.

The studies were conducted in male Swiss mice, aged between 10 and 14 weeks, kept in an air-conditioned room under a constant temperature of 24° C. and ambient conditions of 12:12 hours in the light-dark cycle.

The diet was classic, with standard commercial feed and water provided ad libitum.

Intestinal mucositis was induced intraperitoneally (i.p.) with 5-FU injection at the 4th, 5th and 6th days in a single dose of 200 mg/kg/day. The degree of the disease was assessed by the diarrhea score daily score of days 0-8.

Each animal was examined twice daily. The severity of diarrhea was classified using the following scale: 0, normal (normal or absent stools); 1, light (soft stool a little wet); 2, moderate (faeces wet and with moderate perianal inflammation and alteration in coat color) and 3 in severe faeces (watery with severe perianal inflammation and alteration in coat color).

The mean values of diarrhea were used to assess the severity of diarrhea (n=5 per group).

Three independent studies have been done:
a) Evaluation of the protective effect of curcuminoids;
b) evaluation of the protective effect of Bd;
c) evaluation of the protective effect of the association of curcuminoids and BD.

Figure 3:
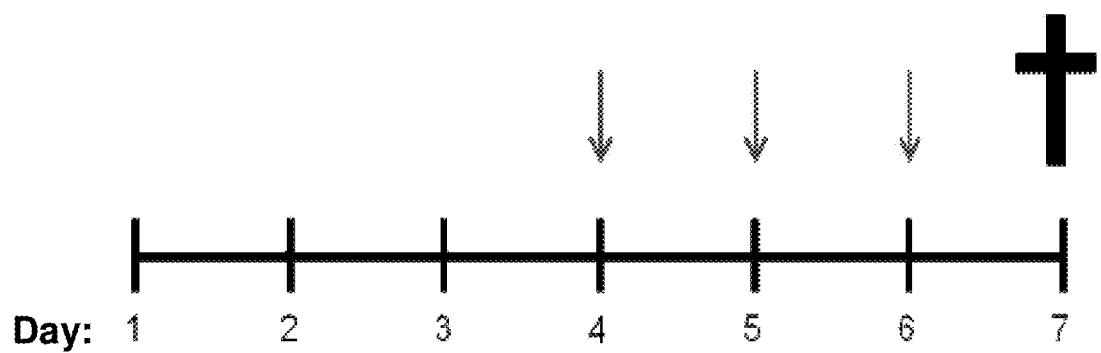
FIG. 3—Treatment scheme of the animals submitted to the study.

The treatments in the 3 studies were performed according to the scheme presented in FIG. 3.

Administration of the test substance for each group was performed orally (gavage) for 6 days, and doses of 5-FU were administered intraperitoneally on the 4th to 6th day.

The first study deals with the evaluation of a formulation containing only curcuminoids. Treatment groups (n=5/group) were thus distributed:
Group I: 3.7 mg/kg curcuminoid+5-FU;
Group II: 7.5 mg/kg curcuminoid+5-FU;
Group III: 15 mg/kg curcuminoid+5-FU;
Group IV: positive control (5-FU);
Group V: negative control (water).

Groups I, II or III received prophylactic treatment with curcuminoids containing formulation and on days 4, 5 and 6 they received a 5-FU injection 4 hours after treatment and were euthanized 24 hours after treatment. The duodenal portion of each animal was extracted and then the paraffin blocks (58-60° C.) were assembled to obtain microscopic images after staining using the Hematoxylin and Eosin technique. In addition, the proliferative effect of the mucosa was evaluated by immunohistochemistry with the cyclin D marker.

In this study, the results showed that the animals treated with the curcuminoids formulation, in a dose-dependent manner, presented a lower weakness with or without diarrhea when compared to the group only exposed to 5-FU. Better results were observed with the dose of 7.5 mg/kg.

Figure 4:
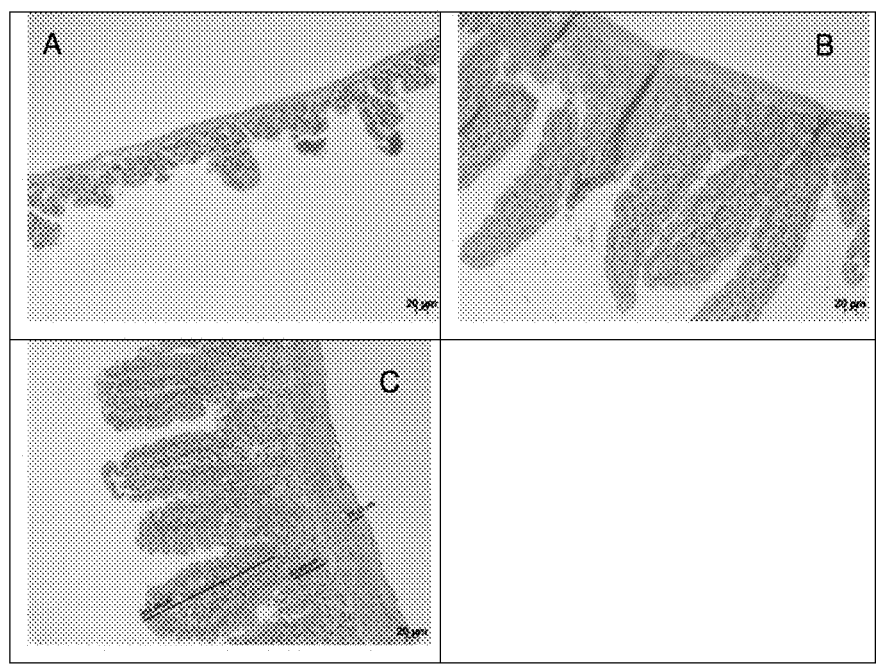
FIG. 4—Histopathological section (eosin-hematoxylin) of the duodenal segment of exposed animal of 5-fluoracil (A); Control animal without treatment (B); And animal treated with formulation containing curcuminoids (7.5 mg/kg) and exposed to 5-fluoracil (C).

The histopathological study (FIG. 4) showed that the exposure of animals to the protocol with 5-FU induces the appearance of mucositis with loss of epithelial lining integrity, blistering, shortening of the crypts and shortening of the villi with the presence of large inflammatory infiltrate (FIG. 4A).

On the other hand, treatment with the formulation of curcuminoids, especially the dose of 7.5 mg/kg preserved the integrity of the epithelium, the crypts and villi, as compared to the normal control, as seen in FIGS. 4B and 4C. We also observed a tendency to increase villus size, suggesting a cellular proliferative stimulating effect.

The second study was carried out with a formulation containing only glycerinated extract of Bd in 3 (three) different doses (75, 100 and 125 mg/kg). The treatment groups (n=5/group) were thus distributed:
Group I: 75 mg/kg Bd+5-FU;
Group II: 100 mg/kg Bd+5-FU;
Group III: 125 mg/kg Bd+5-FU;
Group IV: positive control (5-FU);
Group V: negative control (water).

Figure 5:
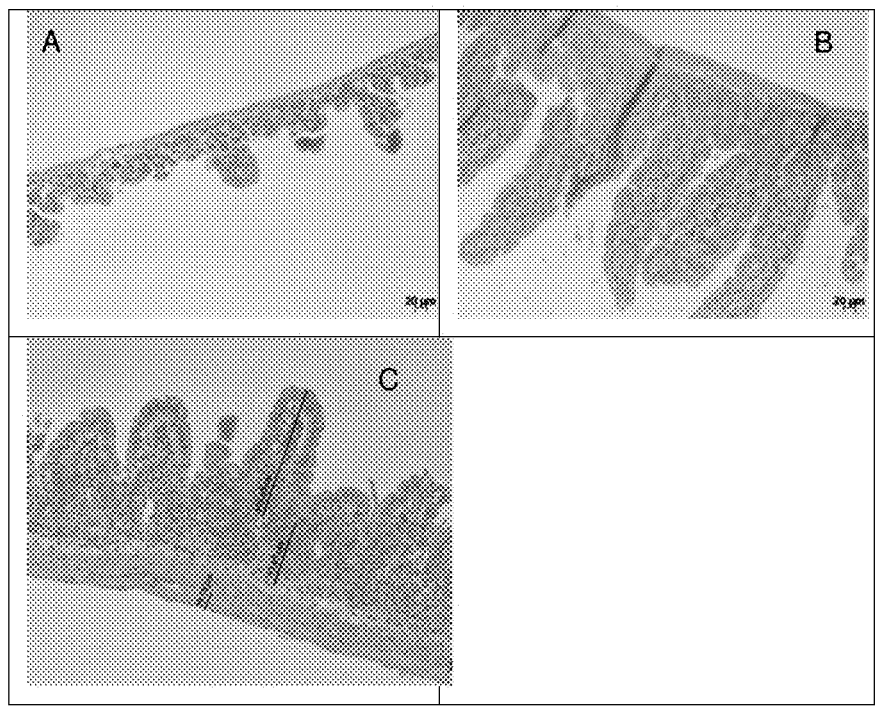
FIG. 5—Histopathological section (eosin-hematoxylin) of the duodenal segment of exposed animal of 5-fluoracil (A); Control animal without treatment (B); And treated with glycerinated extract of *Bidens pilosa* (125 mg/kg) and exposed to 5-fluoracil (C).

The results obtained in this study demonstrated that the glycerinated extract of Bd was effective to protect against the induction of mucositis by 5-FU in a dose-dependent manner. The histopathological study seen in FIG. 5 showed, as previously described, that exposure to 5-FU induces a severe mucositis. On the other hand, treatment with glycerinated extract of Bd, in particular the 125 mg/kg dose, preserved the integrity of the epithelium, crypts and villi when compared to normal control (FIGS. 5B and 5C).

The third study sought to evaluate a formulation with the association of curcuminoids (75 mg/kg) and Bd (125 mg/kg) (CBd). Treatment groups (n=5/group) were thus distributed:
Group I: CBd+5-FU;
Group II: CBd+5-FU;
Group III: CBd+5-FU;
Group IV: positive control (5-FU);
Group V: negative control (water).

In this study the results showed, in addition to the results reported above with the treatment of the substances alone, a drastic reduction of the inflammatory infiltrate with an increase in cell profiling, that is, the association promoted a protective effect superior to the isolated effect of curcuminoids and Bd against Mucositis.

Figure 6:
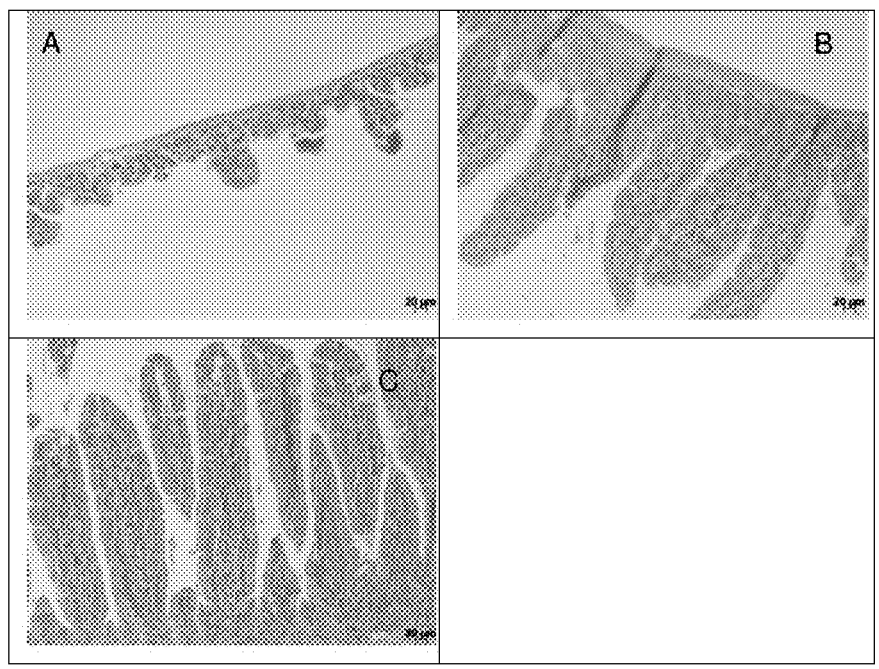
FIG. 6—Histopathological section (eosin-hematoxylin) of the duodenal segment of exposed animal of 5-fluoracil (A); Control animal without treatment (B); And animals treated with mucoadhesive formulation and curcuminoids (7.5 mg/kg) plus *Bidens pilosa* (125 mg/kg) and exposed to 5-fluoracil (C).

Histopathological cut showed a reduction of local inflammation and with cellular hyperproliferation demonstrated by the increase of crypts and villi in the animals treated with the combination (FIG. 6C).

From these animals, peripheral blood samples were collected by retro-orbital puncture. Serum IL-1β levels were analyzed by ELISA kits for IL-1β dosing according to the manufacturer's instructions.

The results demonstrated that the induction of mucositis in animals exposed to 5-FU produced a significant increase of IL-1β in the control animals. However, the animals treated with the formulation containing the combination of curcuminoids (7.5 mg/kg) and Bd (125 mg/kg) (CBd), levels of IL-1β were similar to those found in control animals. Studies carried out with formulation containing only curcumin or containing only Bd, also reduced IL-1β levels, but much less effectively. This suggested a superior effect of the association of assets. This result further suggests a reduction in apoptosis in the epithelial cells induced by the drug. In addition, in animals treated with the CBd formulation the severity of mucositis was lower when compared to the control group.

The present invention is directed to the use of the formulation containing the combination of curcuminoids from *Curcuma longa* and *Bidens pilosa* for the treatment of mucosal diseases, for example mucositis of the gastrointestinal tract induced by radio and/or chemotherapy, based on formulation Pharmaceutical product with mucoadhesive properties, controlled release that will provide an additional prophylactic and/or therapeutic alternative to the treatments used in the medical clinic.

BIBLIOGRAPHIC REFERENCES

1. Armstrong J A, McCaffrey R. The effects of mucositis on quality of life in patients with head and neck cancer. Clin J Oncol Nurs. 2006; 10(1):53-6.
2. Carl W. Oral complications of local and systemic cancer treatment. Curr Opin Oncol. 1995; 7(4):320-4.
3. Corren J, Lemay M, Lin Y, Rozga L, Randolph R K. Clinical and biochemical effects of a combination botanical product (ClearGuard) for allergy: a pilot randomized double-blind placebo-controlled trial. Nutr J. 2008 Jul. 14; 7:20.
4. Costa Rde J, Diniz A, Mantovani M S, Jordão B Q. In vitro study of mutagenic potential of *Bidens pilosa* Linné and Mikania glomerata Sprengel using the comet and micronucleus assays. J Ethnopharmacol. 2008 Jun. 19; 118(1): 86-93.
5. Dadhaniya P, Patel C, Muchhara J, Bhadja N, Mathuria N, Vachhani K, Soni M G. Safety assessment of a solid lipid curcumin particle preparation: Acute and subchronic toxicity studies. Food Chem Toxicol. 2011 May 6.
6. Epstein J B, Schubert M M. Oropharyngeal mucositis in cancer therapy. Review of pathogenesis, diagnosis, and management. Oncology. 2003; 17(12):1767-79.
7. Fall-Dickson J M, Ramsay E S, Castro K, Woltz P, Sportés C. Oral mucositis-related oropharyngeal pain and correlative tumor necrosis factor-alpha expression in adult oncology patients undergoing hematopoietic stem cell transplantation. Clin Ther. 2007; 29 Suppl:2547-61.
8. Köstler W J, Hejna M, Wenzel C, Zielinski C C. Oral mucositis complicating chemotherapy and/or radiotherapy: options for prevention and treatment. CA Cancer J Clin. 2001; 51(5):290-315.
9. Logan R M, Stringer A M, Bowen J M, Yeoh A S, Gibson R J, Sonis S T, Keefe D M.
10. Lüer S, Troller R, Jetter M, Spaniol V, Aebi C Topical curcumin can inhibit deleterious effects of upper respiratory tract bacteria on human oropharyngeal cells in vitro: potential role for patients with cancer therapy induced mucositis? Support Care Cancer. 2011 June; 19(6):799-806.
11. Meirovitz A, Kuten M, Billan S, Abdah-Bortnyak R, Sharon A, Peretz T, Sela M, Schaffer M, Barak V. Cytokines levels, severity of acute mucositis and the need of PEG tube installation during chemo-radiation for head and neck cancer—a prospective pilot study. Radiat Oncol. 2010 Feb. 25; 5:16
12. Peterson D E. Research advances in oral mucositis. Curr Opin Oncol. 1999 July; 11(4):261-6.
13. Pico J L, Avila-Garavito A, Naccache P Mucositis: Its Occurrence, Consequences, and Treatment in the Oncology Setting. Oncologist. 1998; 3(6):446-51.
14. Carl W. Oral complications of local and systemic cancer treatment. Curr Opin Oncol. 1995; 7(4):320-4.
15. Rubenstein E B, Peterson D E, Schubert M, Keefe D, McGuire D, Epstein J, Elting L S, Fox P C, Cooksley C, Sonis S T; Clinical practice guidelines for the prevention and treatment of cancer therapy-induced oral and gastrointestinal mucositis. Cancer. 2004; 100(9):2026-46.
16. Sonis S T, Elting L S, Keefe D, Peterson D E, Schubert M, Hauer-Jensen M, Bekele B N, Raber-Durlacher J, Donnelly J P, Rubenstein E B; Perspectives on cancer therapy-induced mucosal injury: pathogenesis, measurement, epidemiology, and consequences for patients. Cancer. 2004; 100(9):1995-2025.
17. Sonis S T, Sonis A L, Lieberman A. Oral complications in patients receiving treatment for malignancies other than of the head and neck. J Am Dent Assoc. 1978; 97(3):468-72.
18. The role of pro-inflammatory cytokines in cancer treatment-induced alimentary tract mucositis: pathobiology, animal models and cytotoxic. Cancer Treat Rev. 2007 August; 33(5):448-60.
19. Vathsala P G, Dende C, Nagaraj V A, Bhattacharya D, Das G, Rangarajan P N, Padmanaban GCurcumin-arteether combination therapy of Plasmodium berghei-infected mice prevents recrudescence through immunomodulation. PLoS One. 2012; 7(1).
20. Vissink A, Burlage F R, Spijkervet F K, Jansma J, Coppes R P. Prevention and treatment of the consequences of head and neck radiotherapy. Crit Rev Oral Biol Med. 2003; 14(3):213-25.
21. Wu Z, Han X, Qin S, Zheng Q, Wang Z, Xiang D, Zhang J, Lu H, Wu M, Zhu S, Yu Y, Wang Y, Han W. Interleukin 1 receptor antagonist reduces lethality and intestinal toxicity of 5-Fluorouracil in a mouse mucositis model. Biomed Pharmacother. 2011 August; 65(5):339-44.
22. Wu Z, Han X, Qin S, Zheng Q, Wang Z, Xiang D, Zhang J, Lu H, Wu M, Zhu S, Yu Y, Wang Y, Han W. Interleukin 1 receptor antagonist reduces lethality and intestinal toxicity of 5-fluorouracil in a mouse mucositis model. Biomed Pharmacother. 2010 November; 64(9):589-93
Wu Z, Han X, Qin S, Zheng Q, Wang Z, Xiang D, Zhang J, Lu H, Wu M, Zhu S, Yu Y, Wang Y, Han W. Interleukin 1 receptor antagonist reduces lethality and intestinal toxicity of 5-Fluorouracil in a mouse mucositis model. Biomed Pharmacother. 2011, 65(5):339-44.
23. Yoshida N, Kanekura T, Higashi Y, Kanzaki T. *Bidens pilosa* suppresses interleukin-1beta-induced cyclooxygenase-2 expression through the inhibition of mitogen activated protein kinases phosphorylation in normal human dermal fibroblasts. J Dermatol. 2006 October; 33(10):676-83.

The invention claimed is:
1. An anti-inflammatory, proliferative, protective and mucoadhesive, soluble and stable pharmaceutical composition comprising:
 i) 1 to 50% by weight of the composition of a mixture of *Curcuma Longa* extract and a *Bidens pilosa* extract as an active ingredient;
 ii) 6 to 55% by weight of the composition of a solvent selected from distilled water, propylene glycol, or polyethylene glycol 400;
 iii) 25 to 35% by weight of the composition of a co-solvent selected from distilled water, propylene glycol or polyethylene glycol 400;
 iv) 15% by weight of the composition of a surfactant selected from poly(oxyethylene), poly(oxypropylene), poloxamer 407, or poloxamer 188;
 v) 0 to 25% by weight of the composition of a carrier selected from distilled water, propylene glycol or polyethylene glycol 400; and
 vi) 0 to 1% by weight of the composition of an antioxidant selected from butylhydroxytoluene, a mixture of sodium bisulfite and sodium metabisulfite, or citric acid.

2. The pharmaceutical composition, according to claim 1 that comprises:
 a mixture of *Curcuma Longa* extract and *Bidens pilosa* extract at a concentration of up to 2.5 mg/mL;
 15% (v/v) distilled water;
 15% (v/v) propylene glycol;
 15% (w/v) poloxamer 407 or poloxamer 188; and
 20% (v/v) polyethylene glycol 400.

3. The pharmaceutical composition according to claim 1 that comprises:
 a mixture of *Curcuma Longa* extract and *Bidens pilosa* extract in the concentration of up to 25 mg/mL;
 20% (v/v) distilled water;
 50% (v/v) propylene glycol;
 15% (w/v) poloxamer 407 or poloxamer 188; and
 30% (v/v) polyethylene glycol 400.

4. The pharmaceutical composition according to claim 1 that comprises:
 *Curcuma Longa* extract at a concentration of up to 25 mg/mL;
 40% (w/w) of *Bidens pilosa* glycerol extract;
 30% (v/v) propylene glycol;
 30% (v/v) of polyethylene glycol 400;
 15% (w/v) poloxamer 407 or poloxamer 188; and
 0.01 to 1% (v/v) sodium bisulfite and butylhydroxytoluene.

5. The pharmaceutical composition according to claim 1 that comprises:
- an extract of *Curcuma Longa* at a concentration of 25 mg/mL;
- 65% (w/w) of *Bidens pilosa* glycerine extract;
- 5% (w/w) of liquid vaseline;
- 3% (w/w) of stearic acid;
- 0.4% (w/w) of cetyl alcohol;
- 0.35% (w/w) of cetostearyl alcohol;
- 3% (w/w) of glyceryl monostearate;
- 1% (w/w) of isopropyl myristate;
- 15% (w/w) of poloxamer 407 or poloxamer 188;
- 6% (w/w) of propylene glycol;
- 0.1% (w/w) of methylparaben;
- 0.05% (w/w) of propylparaben; and
- 0.05% (w/w) of butylhydroxytoluene;

wherein the composition is semi-solid.

6. The pharmaceutical composition according to claim 1 that is in a solid tablet form and comprises:
- 25 to 200 mg per tablet of *Curcuma Longa* extract;
- 35% to 45% (w/w) of *Bidens pilosa* glycerine extract;
- 250 to 350 mg per tablet of mannitol;
- 100 to 140 mg per tablet of poloxamer 407 or poloxamer 188;
- 200 to 400 mg per tablet of microcrystalline cellulose;
- 5 to 15 mg per tablet of sodium metabisulfite; and
- 20 to 40 mg per tablet of citric acid.

* * * * *